US010973595B2

(12) United States Patent
Mewes et al.

(10) Patent No.: US 10,973,595 B2
(45) Date of Patent: Apr. 13, 2021

(54) DEVICE AND METHOD FOR CONTROLLING A SYSTEM COMPRISING AN IMAGING MODALITY

(71) Applicant: Siemens Healthcare GmbH, Erlangen (DE)

(72) Inventors: Philip Mewes, Nuremberg (DE); Peter Mountney, London (GB); Manish Sahu, Berlin (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 334 days.

(21) Appl. No.: 15/749,795

(22) PCT Filed: Aug. 5, 2016

(86) PCT No.: PCT/EP2016/068736
§ 371 (c)(1),
(2) Date: Feb. 2, 2018

(87) PCT Pub. No.: WO2017/025456
PCT Pub. Date: Feb. 16, 2017

(65) Prior Publication Data
US 2018/0228558 A1 Aug. 16, 2018

(30) Foreign Application Priority Data
Aug. 13, 2015 (EP) .................................... 15180955

(51) Int. Cl.
*A61B 34/30* (2016.01)
*A61B 34/00* (2016.01)
(Continued)

(52) U.S. Cl.
CPC ............ *A61B 34/30* (2016.02); *A61B 1/0005* (2013.01); *A61B 6/463* (2013.01); *A61B 34/25* (2016.02)

(58) Field of Classification Search
CPC ......... A61B 34/25; A61B 34/30; A61B 34/32; A61B 34/35; A61B 34/37;
(Continued)

(56) References Cited

U.S. PATENT DOCUMENTS

2008/0091302 A1    4/2008  Sholev
2009/0036902 A1    2/2009  DiMaio
(Continued)

FOREIGN PATENT DOCUMENTS

CN    101184429 A    5/2008
CN    102958464 A    3/2013
(Continued)

OTHER PUBLICATIONS

Chinese Office Action and English translation thereof dated Mar. 2, 2020.
(Continued)

*Primary Examiner* — Diane D Yabut
*Assistant Examiner* — Christian D Knauss
(74) *Attorney, Agent, or Firm* — Harness, Dickey & Pierce, P.L.C.

(57) ABSTRACT

A method is for controlling a system including an imaging modality. The method includes receiving an image and/or a series of images of a portion of a patient from the imaging modality, the field of view of the image and/or of the series of images covering at least a part of an instrument; determining whether the part of the instrument is located within a defined portion of the field of view and/or in a given state selected from a plurality of first states and/or the part of the instrument executes a given movement selected from a plurality of movements; and generating a control command for performing an action depending on whether the part of the instrument is located within the defined portion of the field of view and/or the part of the instrument is in the given
(Continued)

state and/or the part of the instrument executes the given movement.

15 Claims, 5 Drawing Sheets

(51) Int. Cl.
*A61B 1/00* (2006.01)
*A61B 6/00* (2006.01)

(58) Field of Classification Search
CPC ........ A61B 2034/252; A61B 2034/254; A61B 2034/256; A61B 2034/258; A61B 2034/301; A61B 2034/302; A61B 2034/303; A61B 2034/304; A61B 2034/305; A61B 2034/306
See application file for complete search history.

(56) References Cited

U.S. PATENT DOCUMENTS

| | | |
|---|---|---|
| 2009/0192524 A1 | 7/2009 | Itkowitz |
| 2011/0118753 A1 | 5/2011 | Itkowitz et al. |
| 2013/0030571 A1 | 1/2013 | Ruiz Morales et al. |
| 2014/0031659 A1* | 1/2014 | Zhao ............... A61B 34/70 606/130 |
| 2014/0055489 A1* | 2/2014 | Itkowitz ........... A61B 34/30 345/633 |
| 2014/0107667 A1* | 4/2014 | Komuro ........... A61B 34/70 606/130 |
| 2014/0228632 A1 | 8/2014 | Sholev et al. |
| 2016/0354166 A1* | 12/2016 | Popovic ........... A61B 1/3132 |

FOREIGN PATENT DOCUMENTS

| | | |
|---|---|---|
| CN | 104473693 A | 4/2015 |
| CN | 104582622 A | 4/2015 |
| WO | WO-2013027201 A2 | 2/2013 |
| WO | WO 2015091226 A1 | 6/2015 |

OTHER PUBLICATIONS

International Search Report PCT/ISA/210 for International Application No. PCT/EP2016/068736 dated Jan. 11, 2017.
Written Opinion of the International Searching Authority PCT/ISA/237 for International Application No. PCT/EP2015/068735 dated Jan. 11, 2017.
Bouarfa, Loubna, et.al.: "In-vivo real-time tracking of surgical instruments in endoscopic video"; in: Minimally Invasive Therapy; vol. 21; pp. 129-134, 2012; 2012.
McMaster-Fay, Roger, Dr.: "What is a laparoscopic hysterectomy?"; in: www.rfay.com.au/laparoscopic.html; 2008.
Kraft, B. M. et al.: "The AESOP robot system in laparoscopic surgery: Increased risk or advantage for surgeon and patient?"; in: Surgical Endoscopy; vol. 18; pp. 1216-1223, 2004; DOI 10.2007 s00464-003-9200-z.
Pietikäinen, Matti, et.al.: "Local Binary Patterns for Still Images", in: Computer Vision Using Local Binary Patterns; vol. 40; pp. 13-48, 2011; ISBN 978-0-85729-747-1.
Freehand 2010 Ltd: "See the News—The Freehand System"; in: http://www.freehandsurgeon.com/.
Storz, Karl: "Holding Systems from Karl Storz", https://www.karlstorz.com/cps/rde/xbcr/karlstorz_assets/ASSETS/3316251.pdf.
Sa-Ing, Vera, et.al.: "Object Tracking for Laparoscopic Surgery Using the Adaptive Mean-Shift Kalman Algorithm"; in: International Journal of Machine Learning and Computing; vol. 1, No. 5; pp. 441-447, 2011.
Mountney, Peter et.al.: "Three-Dimensional Tissue Deformation Recovery and Tracking"; in: IEEE Signal Processing Magazine; pp. 14-24; 2010.
Hourlay, P.: "How to Maintain the Quality of Laparoscopic Surgery in the Era of Lack of Hands?"; in: Acta Chirurgica Belgica; vol. 106, No. 1; pp. 22-26, 2006.
Buess G. F. et. al.: "A new remote-controlled endoscope positioning system for endoscopic solo surgery", in: Surgical Endoscopy, 2000, vol. 14, pp. 395-399.
Taniguchi, Kazuhiro et al.: "Method for objectively evaluating psychological stress resulting when humans interact with robots"; in: INTECH Open Access Publisher, pp. 141-165.
Office Action for Chinese Patent Application No. 2016800478631 dated Oct. 16, 2020 and English translation thereof.

* cited by examiner

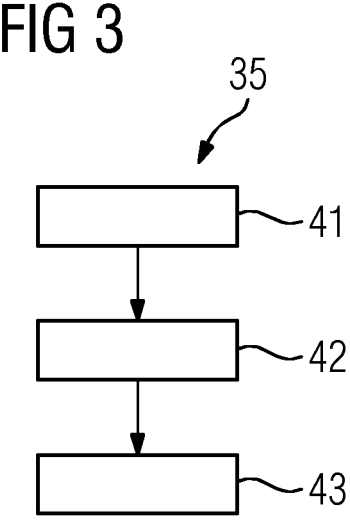
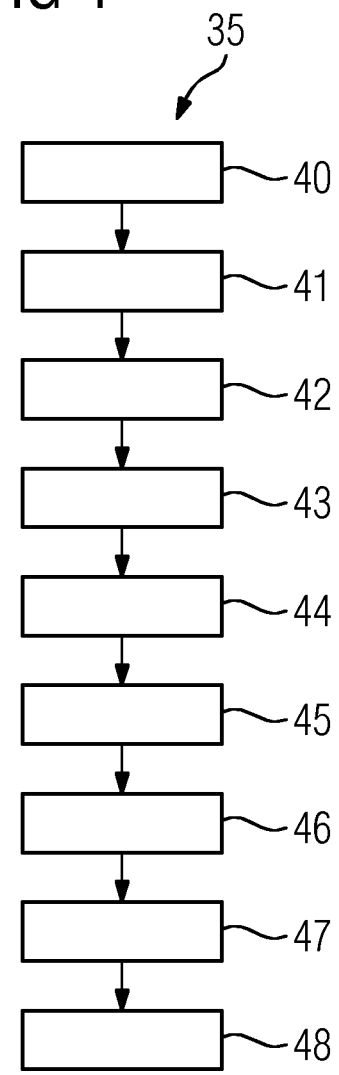

DEVICE AND METHOD FOR CONTROLLING A SYSTEM COMPRISING AN IMAGING MODALITY

PRIORITY STATEMENT

This application is the national phase under 35 U.S.C. § 371 of PCT International Application No. PCT/EP2016/068736 which has an International filing date of Aug. 5, 2016, which designated the United States of America and which claims priority to European patent application number EP 15180955.5 filed Aug. 13, 2015, the entire contents of which are hereby incorporated herein by reference.

FIELD

The invention generally relates in one embodiment to a method and/or device for controlling a system comprising an imaging modality. In another embodiment, the invention relates to a system comprising an imaging modality.

BACKGROUND

Minimal invasive surgery (MIS) or laparoscopic surgery has become popular because of its advantages over the conventional open surgery. In MIS, surgeons treat a lesion inside the human body through small incisions, which cause less pain and allow faster recovery. During surgery, an assistant is usually required to hold the endoscope/laparoscope in order to adapt its field of view to the anatomical and interventional situation, which may have certain drawbacks, e.g. trembling of the hand of the assistant cause image blurring resulting in eyestrain and concentration problems for the surgeons and/or costs of a second physician.

A passive holder or robotic holder of the laparoscope could overcome some of this problem. However in a (cost efficient) scenario where only one physician is required for the entire procedure (a so called "solo-surgery" scenario) using a passive holder, the "solo" surgeon is required to release his hands from his surgical instruments in order to adjust the passive holder for each change of the laparoscopic viewing position. Depending on the surgical procedure, this may be difficult or even impossible.

A robotic system may overcome this problem, when the surgeon is able to provide positioning commands to the robotic holder without using its hands. The communication between the robotic system and the surgeons is however a sensible part of a such as system since it needs to be intuitive, fast, reliable and very safe given the sensible environment such a robotic device is working in.

Passive laparoscopic holders are widely using in surgery and are commercially available (e.g. ENDOCRANE from Karl Storz).

Robotic holders that provide human-machine interfaces that are suitable for solo surgery are also commercially available or have been presented in literature. Often they require additional hardware to establish a reliable human machine interface to the robot, e.g. food pedal, voice control (e.g. Buess, G. F., A. Arezzo, M. O. Schurr, F. Ulmer, H. Fisher, L. Gumb, T. Testa, and C. Nobman. "A new remote-controlled endoscope positioning system for endoscopic solo surgery." Surgical endoscopy 14, no. 4 (2000): 395-399.), or tracking systems.

SUMMARY

The underlying technical problem of at least one embodiment of the invention is to facilitate an improved controlling of a system comprising an imaging modality.

At least one embodiment of the invention is directed to a method, a device, a system, a computer program product and/or a machine-readable medium. Further claims are related to further embodiments of the invention.

The invention relates, in one embodiment, to a method for controlling a system including an imaging modality, the method comprising Receiving an image and/or a series of images of a portion of a patient from the imaging modality, the field of view of the image and/or of the series of images covering at least a part of an instrument, Determining whether the part of the instrument is located within a predefined portion of the field of view and/or whether the part of the instrument is in a given state selected from a plurality of predefined first states and/or whether the part of the instrument executes a given movement selected from a plurality of predefined movements, and Generating a control command for performing a predefined action of an action unit of the system depending on whether the part of the instrument is located within the predefined portion of the field of view and/or whether the part of the instrument is in the given state selected from the plurality of predefined first states and/or whether the part of the instrument executes the given movement selected from the plurality of predefined movements.

The invention relates in one embodiment to a device comprising:

a receiving unit for receiving an image of a portion of a patient, the field of view of the image covering at least a part of an instrument, a first determining unit for determining whether the part of the instrument is located within a predefined portion of the field of view and/or whether the part of the instrument is in a given state selected from a plurality of predefined first states, and a generating unit for generating a control command for performing a predefined action depending on whether the part of the instrument is located within the predefined portion of the field of view and/or whether the part of the instrument is in the given state selected from the plurality of predefined first states.

The invention relates in one embodiment to a system comprising the device according to any one of the embodiments of the invention described herein, an action unit for performing the predefined action based on the control command received from the generating unit of the device, and an imaging modality, wherein the image is received from the imaging modality.

The invention relates in one embodiment to a computer program product comprising a computer program, the computer program being loadable directly into a memory unit of a control unit of the system according to any one of the embodiments of the invention described herein, including program code sections to make the system execute the method according to any one of the embodiments of the invention described herein when the computer program is executed in the control unit.

The invention relates in one embodiment to a machine-readable medium, on which program code sections of a computer program are saved, the program code sections being loadable directly into and/or executable in a processing unit of a control unit of the system according to any one of the embodiments of the invention described herein to make the system execute the method according to any one of the embodiments of the invention described herein when the program code sections are executed in the processing unit.

In one embodiment of the invention, the inventors propose a way of providing positioning commands to a robotic laparoscopic holder using a specific propriety of an instrument, wherein at least a part of the instrument is covered by the field of view of the laparoscopic image. Therefore a surgical instrument already introduced in the human body cavity can be used to provide an intuitive human-machine interface to the physician. No additional hardware is necessary.

In another embodiment of the invention, the inventors propose to use a surgical instrument as a pointer element of a graphical user interface with the following steps:

A rigid laparoscope (or similar viewing device) is mounted on a robot and introduced into a patient, A surgical instrument (or a specifically for the purpose of this idea manufactured device) is introduced into the patient and is made visible on the laparoscopic image by the surgeon, The laparoscopic image is overlay with the graphical user interface, The surgical instrument points to one specific element of the graphical user interface, The robot performs a motion or other actions, such as switch of modes or activation of other acutators, that is associated with the specific control element.

The invention relates, in one embodiment, to a method for controlling a system including an imaging modality, the method comprising Receiving an image and/or a series of images of a portion of a patient from the imaging modality, the field of view of the image and/or of the series of images covering at least a part of an instrument, Determining whether the part of the instrument is located within a predefined portion of the field of view and/or whether the part of the instrument is in a given state selected from a plurality of predefined first states and/or whether the part of the instrument executes a given movement selected from a plurality of predefined movements, and Generating a control command for performing a predefined action of an action unit of the system depending on whether the part of the instrument is located within the predefined portion of the field of view and/or whether the part of the instrument is in the given state selected from the plurality of predefined first states and/or whether the part of the instrument executes the given movement selected from the plurality of predefined movements.

The invention relates in one embodiment to a method, wherein the predefined portion of the field of view is selected from a plurality of predefined portions of the field of view, wherein each portion of the plurality of predefined portions of the field of view is assigned to one of a plurality of different predefined actions.

The invention relates in one embodiment to a method, the method comprising:

Displaying the image on a display device.

The invention relates in one embodiment to a method, the method comprising:

Highlighting the predefined portion of the field of view and/or each portion of the plurality of predefined portions of the field of view.

The invention relates in one embodiment to a method, the method comprising:

Displaying a first information in the displayed image, the first information indicating the predefined action to which the highlighted predefined portion of the field of view is assigned.

The invention relates in one embodiment to a method, the method comprising:

Displaying a second information in the displayed image, the second information regarding the location of the part of the instrument and/or a given state selected from the plurality of predefined first states.

The invention relates in one embodiment to a method, the part of the instrument comprising a plurality of components, wherein each state of the plurality of predefined first states is assigned to one of a plurality of different positions and/or orientations of the components relative to each other and/or wherein each movement of the plurality of predefined movements is assigned to one of a plurality of different movements of the components relative to each other.

The invention relates in one embodiment to a method, the instrument comprising a grasper and/or a scissor, the plurality of predefined first states comprising an open state of the grasper and/or the scissor and a closed state of the grasper and/or the scissor and/or the plurality of predefined movements comprising an opening movement of the grasper and/or the scissor and a closing movement of the grasper and/or the scissor.

The invention relates in one embodiment to a method, wherein the predefined action includes changing a condition that is related to an acquisition of the image.

The invention relates in one embodiment to a method, wherein the predefined action includes changing a condition that is selected from the group consisting of the field of view of the image, an angle of view of the image, a zoom of the image, a resolution of the image, a focus of the image, a position of an imaging data acquisition component of the imaging modality relative to the portion of the patient and/or relative to the part of the instrument, an orientation of the imaging data acquisition component of the imaging modality relative to the portion of the patient and/or relative to the part of the instrument and combinations thereof.

The invention relates in one embodiment to a method, the action unit comprising the imaging modality and/or a positioning device for positioning and/or orienting an imaging data acquisition component of the imaging modality relative to the portion of the patient and/or relative to the part of the instrument.

The invention relates in one embodiment to a method, the method comprising:

Superimposing a graphical user interface of the action unit on the image, the highlighted predefined portion of the field of view representing a control element of the graphical user interface regarding the predefined action.

The invention relates in one embodiment to a method, the part of the instrument representing a pointer element of the graphical user interface.

The invention relates in one embodiment to a method, wherein the imaging modality is selected from the group consisting of an optical imaging modality, a laparoscopic imaging modality, an endoscopic imaging modality and an x-ray imaging modality and/or wherein the imaging data acquisition component is selected from the group consisting of a camera, a laparoscope, an endoscope and an x-ray detector.

The invention relates in one embodiment to a method, the method comprising

Determining whether an operating element of the system is in a given state selected from a plurality of predefined second states, Executing further steps of the method depending on whether the operating element is in the given state selected from the plurality of predefined second states.

In one embodiment of the invention the instrument is a surgical instrument. In one embodiment of the invention the part of the instrument is a tip and/or head of the instrument. The invention relates in one embodiment to a method, the method comprising determining whether the part of the instrument executes a given movement selected from a plurality of predefined movements throughout the series of the images.

The invention relates in one embodiment to a method, the method comprising generating a control command for performing a predefined action of an action unit of the system depending on whether the part of the instrument executes the given movement selected from the plurality of predefined movements throughout the series of the images.

The invention relates in one embodiment to a device comprising:
a receiving unit for receiving an image of a portion of a patient, the field of view of the image covering at least a part of an instrument,
a first determining unit for determining whether the part of the instrument is located within a predefined portion of the field of view and/or whether the part of the instrument is in a given state selected from a plurality of predefined first states,
a generating unit for generating a control command for performing a predefined action depending on whether the part of the instrument is located within the predefined portion of the field of view and/or whether the part of the instrument is in the given state selected from the plurality of predefined first states.

The invention relates in one embodiment to a device for executing the method according to any one of the embodiments of the invention described herein.

The invention relates in one embodiment to a system comprising
the device according to any one of the embodiments of the invention described herein,
an action unit for performing the predefined action based on the control command received from the generating unit of the device, and
an imaging modality, wherein the image is received from the imaging modality.

The invention relates in one embodiment to a system, the action unit comprising the imaging modality and/or a positioning device for positioning and/or orienting an imaging data acquisition component of the imaging modality relative to the portion of the patient and/or relative to the part of the instrument.

In one embodiment of the invention the imaging modality and/or the positioning device perform the predefined action.

The invention relates in one embodiment to a system for executing the method according to any one of the embodiments of the invention described herein.

The invention relates in one embodiment to a computer program product comprising a computer program, the computer program being loadable directly into a memory unit of a control unit of the system according to any one of the embodiments of the invention described herein, including program code sections to make the system execute the method according to any one of the embodiments of the invention described herein when the computer program is executed in the control unit.

The invention relates in one embodiment to a machine-readable medium, on which program code sections of a computer program are saved, the program code sections being loadable directly into and/or executable in a processing unit of a control unit of the system according to any one of the embodiments of the invention described herein to make the system execute the method according to any one of the embodiments of the invention described herein when the program code sections are executed in the processing unit.

In one embodiment of the invention the positioning device comprises a robot and/or a robotic laparoscopic holder.

In one embodiment of the invention the positioning device is a robot and/or a robotic laparoscopic holder.

In one embodiment of the invention, the inventors propose a way of providing positioning commands to a robotic laparoscopic holder using a specific propriety of an instrument, wherein at least a part of the instrument is covered by the field of view of the laparoscopic image. Therefore a surgical instrument already introduced in the human body cavity can be used to provide an intuitive human-machine interface to the physician. No additional hardware is necessary.

In many cases, the area of focus of the surgeon is around the location of the head of the surgical instruments. Therefore, the tip/head of the surgical instrument could act like a computer mouse and/or a pointer element of a graphical user interface. Based on its position and/or gestures, control commands can be generated for performing a predefined action of an action unit of the system. For example Opening/Closing of surgical graspers and/or scissors are among two of such gestures.

In another embodiment of the invention, the inventors propose to use a surgical instrument as a pointer element of a graphical user interface with the following steps:
A rigid laparoscope (or similar viewing device) is mounted on a robot and introduced into a patient,
A surgical instrument (or a specifically for the purpose of this idea manufactured device) is introduced into the patient and is made visible on the laparoscopic image by the surgeon,
The laparoscopic image is overlay with the graphical user interface,
The surgical instrument points to one specific element of the graphical user interface,
The robot performs a motion or other actions, such as switch of modes or activation of other acutators, that is associated with the specific control element.

In another embodiment of the invention, the instrument or industrial tool can only be used as a pointer element, when the tool is in a specific state, e.g. the grasper of a surgical tool is open.

In one embodiment of the invention the graphical user interface is a control interface of the action unit and/or a virtual control interface of the action unit.

In another embodiment of the invention, at least one step of the method or the entire process can be activated or deactivated by the surgeon using the operating element. The operating element can be for example a foot switch and/or a safety switch.

In one embodiment, the invention enables the utilization of a surgical instrument as a pointer element in conjunction with a graphical user interface superimposed on a laparoscopic image, e.g. of the inside of the human body cavity, to control the movement of a robotic laparoscopic holder. In one embodiment, the invention enables using existing mechanically modifiable, e.g. from outside the human body cavity, states, e.g. grasper open or closed states, of a surgical instruments to trigger, alter, active or deactivate a control element of the graphical user interface and/or a predefined action of an action unit.

BRIEF DESCRIPTION OF THE DRAWINGS

Example embodiments of the invention will be illustrated below with reference to the accompanying figures. The illustration in the figures is schematic and highly simplified and not necessarily to scale.

In the drawings:

FIG. 3 shows a device according to one embodiment of the invention, FIG. 4 shows a device according to one embodiment of the invention.

DETAILED DESCRIPTION OF THE EXAMPLE EMBODIMENTS

Figure 1:
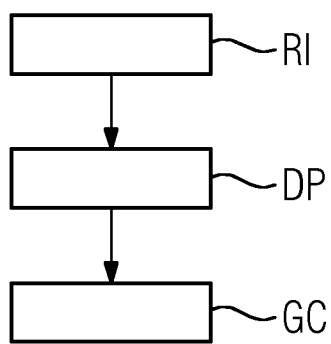
FIG. 1 shows a diagram illustrating a method according to one embodiment of the invention.

FIG. 1 shows a diagram illustrating a method according to one embodiment of the invention, the method comprising the following steps:

Receiving RI an image 50 and/or a series of images 50 of a portion of a patient 13 from the imaging modality 3, 34, the field of view of the image 50 and/or of the series of images 50 covering at least a part 21 of an instrument 20, Determining DP whether the part 21 of the instrument 20 is located within a predefined portion 51, 52, 53 of the field of view and/or whether the part 21 of the instrument 20 is in a given state selected from a plurality of predefined first states and/or whether the part 21 of the instrument 20 executes a given movement selected from a plurality of predefined movements, Generating GC a control command for performing a predefined action of an action unit 3, 34, 5 of the system 1 depending on whether the part 21 of the instrument 20 is located within the predefined portion 51, 52, 53 of the field of view and/or whether the part 21 of the instrument 20 is in the given state selected from the plurality of predefined first states and/or whether the part 21 of the instrument 20 executes the given movement selected from the plurality of predefined movements.

Figure 2:
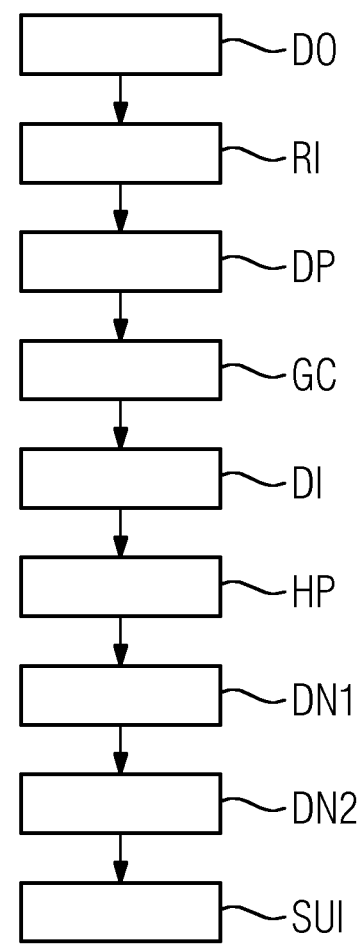
FIG. 2 shows a diagram illustrating a method according to one embodiment of the invention.

FIG. 2 shows a diagram illustrating a method according to one embodiment of the invention, the method comprising the steps RI, DP and GC and the following steps:

Determining DO whether an operating element 37 of the system 1 is in a given state selected from a plurality of predefined second states, Displaying DI the image 50 on a display device 39.

Highlighting HP the predefined portion 51, 52, 53 of the field of view and/or each portion of the plurality of predefined portions 51, 52, 53 of the field of view, Displaying DN1 a first information N1 in the displayed image 50, the first information N1 indicating the predefined action to which the highlighted predefined portion 51, 52, 53 of the field of view is assigned, Displaying DN2 a second information N2 in the displayed image 50, the second information N2 regarding the location of the part 21 of the instrument 20 and/or a given state selected from the plurality of predefined first states, and Superimposing SUI a graphical user interface 55 of the action unit 3, 34, 5 on the image 50, the highlighted predefined portion 51, 52, 53 of the field of view representing a control element of the graphical user interface 55 regarding the predefined action.

FIG. 3 shows a device 35 comprising:

a receiving unit 41 for receiving RI an image 50 of a portion of a patient 13, the field of view of the image 50 covering at least a part 21 of an instrument 20, a first determining unit 42 for determining DP whether the part 21 of the instrument 20 is located within a predefined portion 51, 52, 53 of the field of view and/or whether the part 21 of the instrument 20 is in a given state selected from a plurality of predefined first states, and a generating unit 43 for generating GC a control command for performing a predefined action depending on whether the part 21 of the instrument 20 is located within the predefined portion 51, 52, 53 of the field of view and/or whether the part 21 of the instrument 20 is in the given state selected from the plurality of predefined first states.

FIG. 4 shows a device 35 comprising the receiving unit 41, first determining unit 42, the generating unit 43, the device 35 further comprising:

a second determining unit 40 for determining DO whether an operating element 37 of the system 1 is in a given state selected from a plurality of predefined second states, a displaying unit 44 for displaying DI the image 50 on a display device 39, a highlighting unit 45 for highlighting HP the predefined portion 51, 52, 53 of the field of view and/or each portion of the plurality of predefined portions 51, 52, 53 of the field of view, a first information displaying unit 46 for displaying DN1 a first information N1 in the displayed image 50, the first information N1 indicating the predefined action to which the highlighted predefined portion 51, 52, 53 of the field of view is assigned, a second information displaying unit 47 for Displaying DN2 a second information N2 in the displayed image 50, the second information N2 regarding the location of the part 21 of the instrument 20 and/or a given state selected from the plurality of predefined first states, and a superimposing unit 48 for superimposing SUI a graphical user interface 55 of the action unit 3, 34, 5 on the image 50, the highlighted predefined portion 51, 52, 53 of the field of view representing a control element of the graphical user interface 55 regarding the predefined action.

Figure 5:
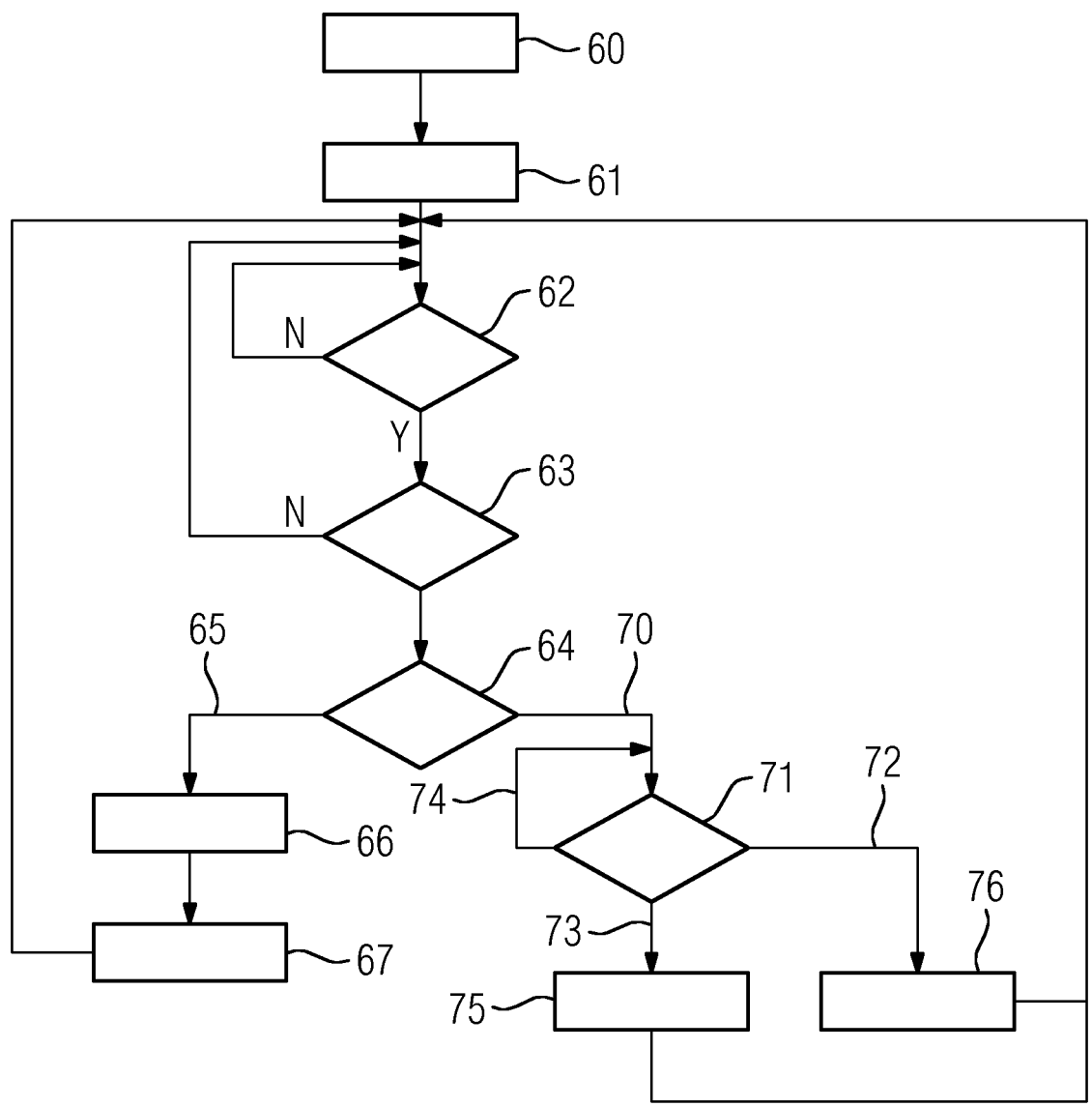
FIG. 5 shows a flow diagram illustrating a method according to one embodiment of the invention.

FIG. 5 shows a flow diagram illustrating a method according to one embodiment of the invention.

Step 60 comprises inserting the laparoscope into the patient. Step 61 comprises inserting the instrument into the patient. Step 62 comprises determining DO whether the operating element 37 of the system 1 is in a given state selected from a plurality of predefined second states. If the operating element 37 is not in the given state selected from the plurality of predefined second states, the corresponding path labeled with "N" is followed returning to step 62. If the operating element 37 is in the given state selected from the plurality of predefined second states, the path labeled with "Y" is followed.

Step 63 comprises determining DP whether the part 21 of the instrument 20 is located within a predefined portion 51 of the field of view. If the part 21 of the instrument 20 is not located within the predefined portion 51 of the field of view, the corresponding path labeled with "N" is followed returning to step 62. If the part 21 of the instrument 20 is located within the predefined portion 51 of the field of view, the path leading to step 64 is followed. Step 64 comprises determining DP whether the part 21 of the instrument 20 is in a given state selected from a plurality of predefined first states.

If the part 21 of the instrument 20 is in a first given state selected from a plurality of predefined first states, the path 65 is followed. If the part 21 of the instrument 20 is in a second given state selected from a plurality of predefined first states, the path 70 is followed. Step 66 comprises locating and/or determining a position and/or a displacement of the part 21 of the instrument 20. Step 67 comprises tracking of the part 21 of the instrument 20. In step 67 the positioning device follows the position and/or the displacement of the part 21 of the instrument 20.

Step 71 comprises determining DP whether the part 21 of the instrument 20 is located within a predefined portion 52, 53 of the field of view. If the part 21 of the instrument 20 is located within portion 52 of the field of view, the path 73 is followed. If the part 21 of the instrument 20 is located within portion 53 of the field of view, the path 72 is followed. Else path 74 is followed.

According to an example embodiment of the invention, Step 75 comprises generating a control command for performing a first predefined action of the action unit 3, 34, 5 of the system 1, wherein the portion 51 is assigned to the first predefined action.

According to an example embodiment of the invention, Step 75 comprises generating a control command for performing a first predefined action of the action unit 3, 34, 5 of the system 1, wherein the portion 52 is assigned to the first predefined action.

According to an example embodiment of the invention, Step 76 comprises generating a control command for performing a second predefined action of the action unit 3, 34, 5 of the system 1, wherein the portion 53 is assigned to the second predefined action. After executing at least one of the steps 67, 75, and 76 a path returning to step 62 is followed. The first predefined action comprises zooming in and/or moving the imaging data acquisition component towards the instrument. The second predefined action comprises zooming out and/or moving the imaging data acquisition component away from the part 21 of the instrument 20.

Figure 6:
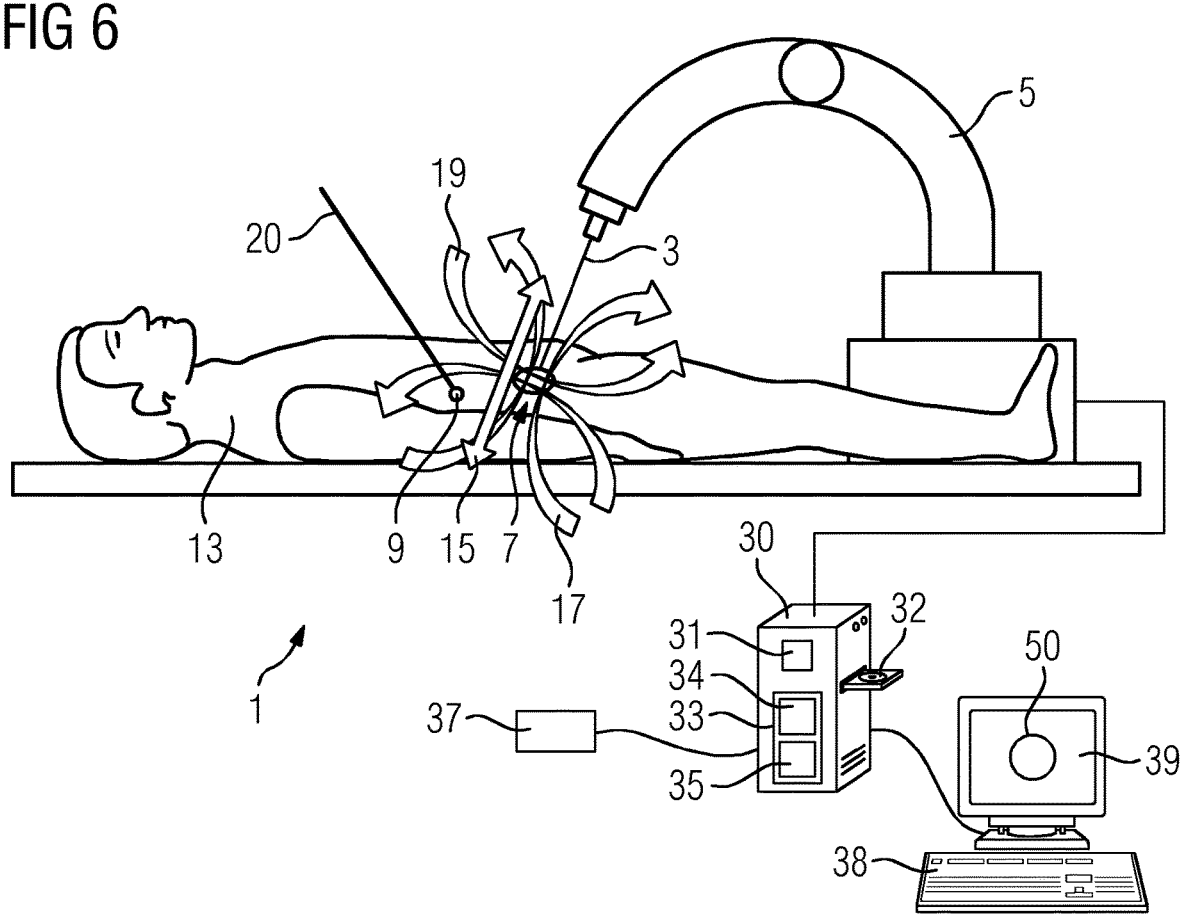
FIG. 6 shows a system according to one embodiment of the invention.

FIG. 6 shows a system according to one embodiment of the invention, the system 1 comprising
the device 35,
an action unit 3, 34, 5 for performing the predefined action based on the control command received from the generating unit 43 of the device 35, and
an imaging modality 3, 34, wherein the image 50 is received from the imaging modality 3, 34.

The system further comprises the control unit 30, the display device 39 and an input device 38 for control inputs. The control unit 30 comprises a processing unit 33. The device 35 and/or one or many or all components of the device 35 are implemented in a processor system of the processing unit 33. The processor system comprises one or several microprocessors. The imaging modality 3, 34 comprises an imaging data acquisition component 3. The imaging modality 3, 34 comprises an imaging modality control unit 34 for controlling the imaging modality 3, 34 and/or the imaging data acquisition component 3.

The arrows 15, 17 and 19 indicate degrees of freedom of a position of the imaging data acquisition component 3 and/or an orientation of the imaging data acquisition component 3. The degree of freedom indicated by the arrow 15 is controlled by an embodiment of the present invention. In the example of FIG. 6, the degrees of freedom indicated by the arrows 17 and 19 are controlled by visual servoing based on tool tracking. The point 9 is a trocar pivot point of the instrument 20. The point 7 is a trocar pivot point of the laparoscope 3.

In the example of FIG. 6, a part of the robot motion, i.e. laparoscopic robot motion, (1 translational, arrow 15 in FIG. 6) is controlled by the above mentioned approach of a surgical instrument as a pointer element.

Another part of the robot motion (2 rotational degrees of freedom, arrows 17 and 19 of FIG. 6) is controlled by simple tool tracking. The surgical tool used in this example is a surgical grasper.

In one embodiment of the invention, the operating element is the "Instrument Track enable" switch. In one embodiment of the invention, the instrument's head position is tracked when the "Instrument Track enable" switch is enabled by the surgeon (e.g. a foot switch). This "Instrument Track enable" switch enhances safety by preventing inadvertent harmful events such as tissue perforation or other collisions. In one embodiment of the invention, the entire process described in the following is only active when this "Instrument Track enable" switch is pressed. Provided, that the "Instrument Track enable" switch is enabled, the tracking would be triggered based on the status of the grasper of the instrument.

Figure 7:
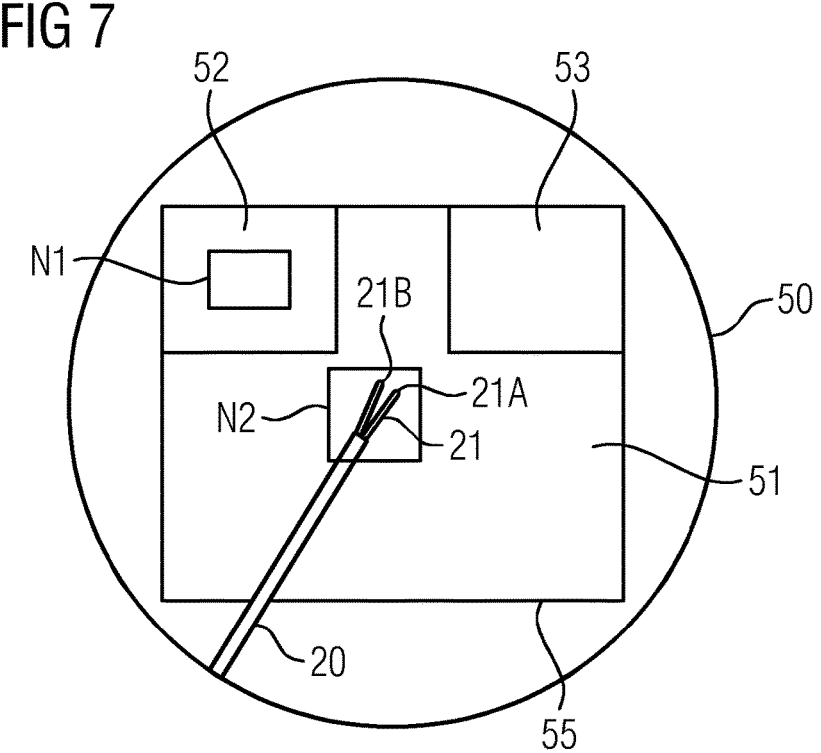
FIG. 7, FIG. 8 and FIG. 9 show and image of a minimally invasive surgery scenario and a graphical user interface.
Figure 8:
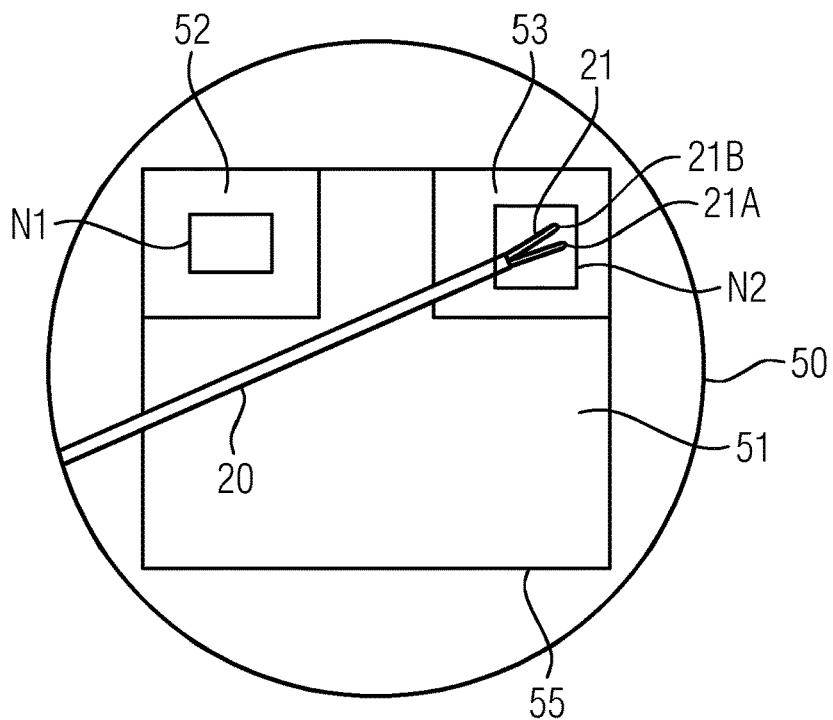
Figure 9:
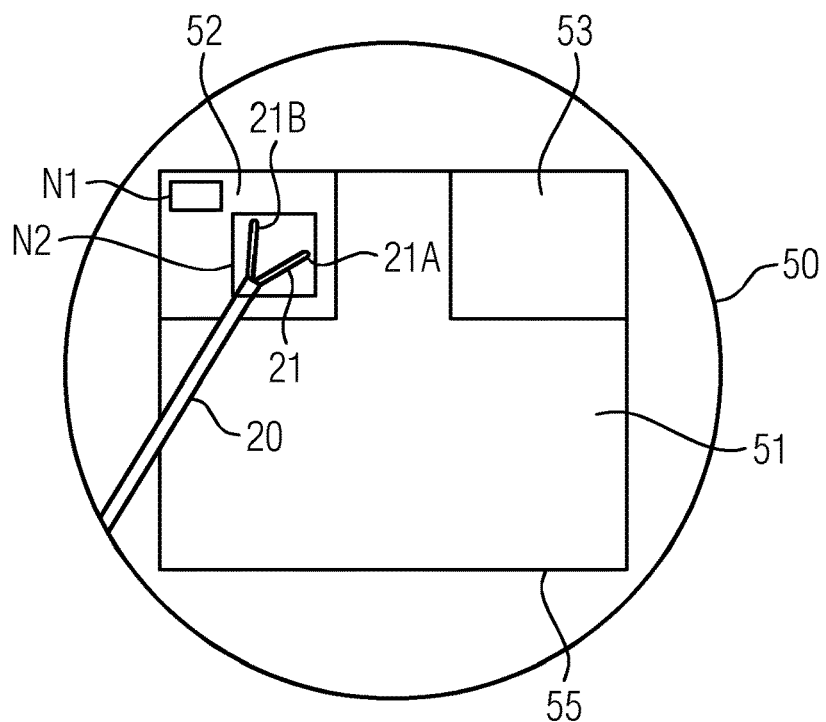

FIG. 7, FIG. 8 and FIG. 9 show and image 50 of a minimally invasive surgery scenario and a graphical user interface 55 of the action unit 3, 34, 5 superimposed on the image 50 according to one embodiment of the invention. The portion 51 comprises the portion 52 and the portion 53.

The part 21 of the instrument 20 is the head of the instrument 20 and a grasper 21 or, equivalent, a gripper 21. In FIG. 7, the grasper is in the closed state. The part 21 of the instrument 20 would be tracked in 2D when the part 21 of the instrument 20 is in the closed state. This results in 2 rotational movements of the robot. As long as the grasper 21 is closed, the robot 5 follows movement of the grasper 21 with 2 rotational degrees if freedom 17, 19. The part 21 of the instrument 20 would not be tracked in 2D, if the grasper is in the open state.

According to an example embodiment of the invention, if the part 21 of the instrument 20 is present in the portions 52 and 53 and the gripper 21 is in the closed state, no predefined action, to which at least one of portion 51 and 52 is assigned, would be performed.

According to an example embodiment of the invention, if the part 21 of the instrument 20 is present in the portions 52 and 53 and the gripper 21 is in the closed state, no predefined action, to which at least one of portion 53 and 52 is assigned, would be performed.

According to an example embodiment of the invention, if the part 21 of the instrument 20 is present in the portion 52 and the gripper 21 is in the closed state, the first predefined action would not be performed.

According to an example embodiment of the invention, if the part 21 of the instrument 20 is present in the portion 53 and the gripper 21 is in the closed state, the second predefined action would not be performed.

E.g. the robot 5 will follow the movement of the part 21 of the instrument 20 using 2 rotational degrees of freedom as indicated by arrows 17 and 19 in FIG. 6. No zooming in or zooming out (i.e. Robot in/out motion) will be performed if the grasper 21 is in the closed state and inside one of portions 52 and portion 53.

For zooming in or out, which in one embodiment of the invention corresponds to kinematically moving the camera 3 towards or away from the part 21 of the instrument 20 and/or the part of the patient 13 with 1 degree of freedom as indicated by the arrow 15 in FIG. 6, there are predefined portions 52, 53 in the image 50 which are assigned to a zooming in action and a zooming out action, respectively. If the instrument gripper 21 is in the open state and the instrument head is present in these zones, the robot 5 would move in and out of the patient.

Zooming in is performed if instrument head 21 is in open state and inside 52. In this case the robot 5 moves the laparoscope 3 towards the part 21 of the instrument 20 and/or the part of the patient 13.

Zooming out is performed if instrument head 21 is in open state and inside 53. In this case the robot 5 moves the laparoscope 3 away from the part 21 of the instrument 20 and/or the part of the patient 13.

The invention claimed is:

1. A method for controlling a system including an imaging modality, the method comprising:
   receiving an image of a portion of a patient from the imaging modality, a field of view of the image covering a part of an instrument;
   determining whether
     the part of the instrument is located within a defined portion of the field of view on the image, and
     the part of the instrument is in a given state selected from a plurality of first states ; and
   generating a control command for performing a defined action, stored in a memory of the system, of at least a component of the imaging modality of the system depending on the determining of whether
     the part of the instrument is located within the defined portion of the field of view, and
     the part of the instrument is in the given state selected from the plurality of first states, wherein the defined portion of the field of view is selected from a plurality of defined portions of the field of view, and wherein each portion of the plurality of defined portions of the field of view is assigned to one of a plurality of different defined actions including the defined action,
   highlighting at least one of the defined portion of the field of view on a display device, and each portion of the plurality of defined portions of the filed of view on a display device,
   superimposing a graphical user interface of the at least a component of the imaging modality on the image, the highlighted portion of the field of view representing a control element of the graphical user interface regarding the defined action, the part of the instrument representing a pointer element of the graphical user interface configured to generate the control command for performing the defined action.

2. The method of claim 1, further comprising:
   displaying the image on the display device.

3. The method of claim 1, further comprising:
   displaying a first information in the image, the first information indicating the defined action, of the plurality of different defined actions, to which the highlighted defined portion of the field of view is assigned.

4. The method of claim 3, further comprising:
   displaying a second information in the image, the second information regarding at least one of
     a location of the at least a part of the instrument and
     a given state selected from the plurality of first states.

5. The method of claim 1, wherein the part of the instrument includes a plurality of components, wherein
   each state of the plurality of first states is assigned to one of a plurality of different positions or
   orientations of the plurality of components relative to each other.

6. The method of claim 1, wherein the instrument includes at least one of a grasper and a scissor, and wherein
   the plurality of first states includes an open state of at least one of the grasper and the scissor and a closed state of at least one of the grasper and the scissor.

7. The method of claim 1, wherein the defined action includes changing a condition related to an acquisition of the image.

8. The method of claim 1, wherein the defined action includes changing a condition that is selected from a group consisting of the field of view of the image, an angle of view of the image, a zoom of the image, a resolution of the image, a focus of the image, a position of an imaging data acquisition component of the imaging modality relative to at least one of the portion of the patient and the part of the instrument, an orientation of the imaging data acquisition component of the imaging modality relative to at least one of the portion of the patient and the part of the instrument.

9. The method of claim 1, wherein the at least a component of the imaging modality includes a positioning device for at least one of positioning and orienting an imaging data acquisition component of the imaging modality relative to at least one of
   the portion of the patient and
   the part of the instrument.

10. The method of claim 9, wherein the positioning device is at least one of a robot and a robotic laparoscopic holder.

11. The method of claim 1, wherein
   the imaging modality is selected from a group consisting of an optical imaging modality, a laparoscopic imaging modality, an endoscopic imaging modality and an x-ray imaging modality and
   an imaging data acquisition component is selected from a group consisting of a camera, a laparoscope, an endoscope and an x-ray detector.

12. The method of claim 1, further comprising
   determining whether a safety switch of the system is in a given state selected from a plurality of second states.

13. The method of claim 1, further comprising:
   highlighting the defined portion of the field of view on the display device.

14. A non-transitory memory of a controller, storing a computer program including program code sections which enable the controller to execute the method of claim 1.

15. A non-transitory machine-readable medium, on which code sections of a computer program are stored, the program code sections being executable by a processor of a controller to execute the method of claim 1.

* * * * *